United States Patent [19]

Turrell et al.

[11] Patent Number: 4,472,833
[45] Date of Patent: Sep. 18, 1984

[54] SPEECH AIDING BY INDICATING SPEECH RATE IS EXCESSIVE

[76] Inventors: Ronald P. Turrell, 23 Pound La., Epsom, Surrey KT18 8RY; John G. Parkhouse, 10 Eastway, Epsom, Surrey KT19 8SG, both of England

[21] Appl. No.: 391,682

[22] Filed: Jun. 24, 1982

[30] Foreign Application Priority Data

Jun. 24, 1981 [GB] United Kingdom ................. 8119390

[51] Int. Cl.³ .......................... A61B 5/12; G09B 19/04
[52] U.S. Cl. ........................................ 381/56; 381/48; 434/185
[58] Field of Search .................. 179/1 F, 1 MN, 1 N, 179/1 SC, 1 VC, 1 SP; 434/185; 73/585; 381/37, 40, 48, 56, 95, 110

[56] References Cited

U.S. PATENT DOCUMENTS

| | | | |
|---|---|---|---|
| 3,773,032 | 11/1973 | Donovan et al. | 179/1 N X |
| 3,972,603 | 8/1976 | Lubinec | 179/1 VC X |
| 4,012,852 | 3/1977 | Journot et al. | 434/185 X |
| 4,143,648 | 3/1979 | Cohen et al. | 179/1 N X |

FOREIGN PATENT DOCUMENTS

| | | | |
|---|---|---|---|
| 2624201 | 12/1977 | Fed. Rep. of Germany | 434/185 |
| 1040001 | 8/1966 | United Kingdom | 179/1 N |
| 521595 | 9/1976 | U.S.S.R. | 179/1 SC |

OTHER PUBLICATIONS

*IBM Technical Disclosure Bulletin*, vol. 4, No. 9, Feb. 1962, p. 38, "Speech Rate Meter" by W. C. Dersch.

*Primary Examiner*—Keith E. George
*Attorney, Agent, or Firm*—Young & Thompson

[57] ABSTRACT

Apparatus and method for aiding speech wherein a signal is provided, representative of detected speech, and is monitored to determine if the speech rate exceeds a predetermined value. If so, then an indication is provided to the speaker. The speech detector can be a microphone (1,2) and the monitoring means (3) preferably drives the indication means in the form of a light source (4), an earphone (7), a meter (5), a loudspeaker (6) or a tactile element. The intensity of the warning indication may increase in proportion to the amount by which the predetermined value is exceeded.

4 Claims, 2 Drawing Figures

SPEECH AIDING BY INDICATING SPEECH RATE IS EXCESSIVE

DESCRIPTION

This invention relates to an apparatus and a method for aiding speech.

It is widely known that nervousness can adversely affect a person's speech and the manner in which some people speak when fearful is very different from the manner in which they speak when calm and relaxed. A speaker who is nervous often speaks too quickly and stumbles over his words, thus communicating his agitation to a listener. A relaxed speaker generally talks more slowly, thus giving himself more time in which to choose his words, and expresses himself more clearly.

The speaker who begins to loose his composure does not easily regain it, because he not only communicates his agitation to a listener but also communicates it back to himself.

Some people who are lacking in confidence are in the habit of speaking badly and this habit tends to be self-perpetuating, in that bad speech destroys confidence. It is very difficult for someone to break a speech habit and, when nervous some people's ability to control their speech is limited. The time to achieve better speech control is in a relaxed atmosphere but, in such circumstances, lack of incentive to control bad speech is a problem.

Whilst sympathetic people can help others to build confidence in their speaking abilities, any speech improvement is generally difficult to maintain without an uncommon degree of perseverance. The present invention is designed to encourage such perseverance to ensure the maintenance of steady measured speech.

Known devices are available to assist in overcoming speech problems, one such device being of the "delayed auditory feedback" type, whereby a speaker has his speech relayed back to himself, via a microphone, a twin-headed type recorder or similar instrument, and earphones. The feedback to the speaker is delayed so that he hears what he has just said, say, a second or less beforehand. This is said to have a stabilising influence upon disfluent speech, a likely explanation being that the speaker is distracted from listening to what he is actually saying by the sound of what he has said an instant previously. Indeed, it has been suggested that one of the causes of disfluency is the intensive initial feedback received by the speaker from listening to his own disfluency.

Another known device for aiding speech is similar to that described above, in that the speaker wears earphones and is distracted from listening to his own speech. This second type of device is known as a "masker", in that the distraction is total, because a loud masking noise is transmitted to the speaker, when vocal activity at the speaker's larynx is detected, thus obliterating all other noise, including that of the speaker's own speech.

Both these known devices, as described above, effect an improvement in speech by weakening or destroying the speaker's auditory feedback. However, they lack any measurement of the speaker's performance and, as a result, provide neither incentive for the speaker to control his speech nor the encouragement of an objective assessment of performance. Also, they are somewhat cumbersome and awkward to use, in that the speaker has to wear earphones.

As indicated above, it is an object of the invention to provide an apparatus and method for aiding speech which, primarily, encourages steady measured speech, and which can be beneficial to anyone who speaks too quickly or who has a speech impediment. Also, it is another object of the invention to provide apparatus which overcomes the disadvantages associated with the known devices described above and which can be used in an unobtrusive manner.

In accordance with one aspect of the invention, there is provided an apparatus for aiding speech, comprising means for detecting speech and for providing a signal representative of said speech, means for monitoring said speech signal and determining the rate thereof, and hence the speech rate, and means for providing an indication when the determined speech signal rate exceeds a predetermined value.

In accordance with another aspect of the invention, there is provided further a method of aiding speech, wherein the speech rate of a speaker is detected and monitored and an indication to the speaker is provided when the speech rate exceeds a predetermined value.

Preferably, said speech detecting means includes a sensor, typically a microphone, which detects speech and transmits a signal, representative of such speech, to a speech rate monitor for determining the speech signal rate and then if such rate exceeds a predetermined value. If so, then an indication possibly in the form of a visual, audible or tactile signal, is given to the speaker who can then adjust his speech rate such that it causes the speech signal rate to fall below the predetermined value, whereby the indication ceases.

The microphone may be of the ordinary type. However, it is important that said monitoring means receives only the speech from a user of the apparatus, in which case, a throat microphone is preferred. Such a microphone, which detects surface vibrations of the user's throat, may be worn by the user such that it is activated by the user's voice only. Alternatively, both an ordinary and a throat microphone could be used in combination, circumstances permitting.

The apparatus may also comprise a pacer which provides the user with an optimum steady beat to encourage the user to speak at a rate which is below the predetermined value at which an indication, that such value has been exceeded, is given.

In order that the invention may be more fully understood, a preferred embodiment of apparatus in accordance therewith, will now be described by way of example and with reference to the accompanying drawings in which.

Figure 1:
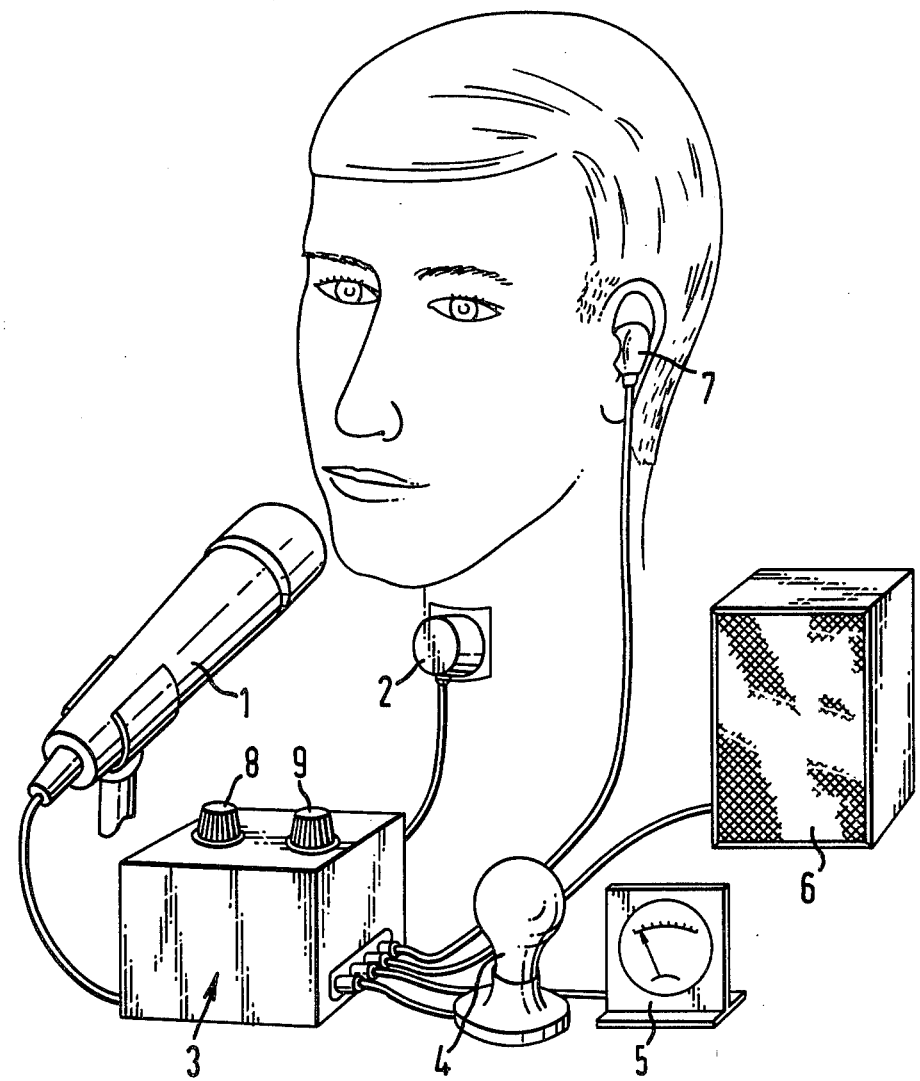
FIG. 1 is a general perspective view of the apparatus in use.

Referring firstly to FIG. 1 of the drawings, an apparatus for aiding speech comprises three basic components, namely:

(a) sensor means in the form of an ordinary microphone 1 and/or a throat microphone 2;

(b) a monitoring unit 3; and (c) indicating means in the form of a light source 4, a meter 5, a loudspeaker 6, an earphone 7 or a tactile indicator (not shown).

Generally speaking, the ordinary microphone 1 and-/or the throat microphone 2 detects a user's speech which is transmitted as a voltage signal to the monitoring unit 3 where the speech signal is monitored and processed to provide a signal representative of the user's speech rate at any one time. The unit 3 then determines whether or not the speech rate is above a predetermined value and, if so, actuates one or more of the indicating means, whereby the user is informed that his speech rate is too high. The intensity of the indication is preferably proportional to the amount by which the speech rate exceeds the predetermined value. As a consequence, the user then reduces his speech rate, and as a result the intensity of the indication reduces proportionally, until it drops below the predetermined value, whereby the indicating means becomes de-activated. The predetermined speech rate value can be adjusted, to suit each individual user, by means of a control knob 8.

The monitoring unit 3 can be provided with an arrangement for producing a pacing signal, usually in the form of a regular series of pulses, which can be transmitted to the user in any suitable form. In this particular instance, the pacing signal is an audible one which is transmitted to the user via the earphone 7. Otherwise, a visual signal, such as that from the light source 4, could be used. This pacing signal provides the user with a regular series of indications as to a preferred rate of speech, which can also be adjusted, to suit the individual, by means of a further control knob 9 at the monitoring unit 3.

The monitoring unit 3 determines the user's speech rate from the signals received from either or both microphone 1,2 and detects this signal as a series of events each representing an entity of speech, for instance, a syllable or other voiced component.

Figure 2:
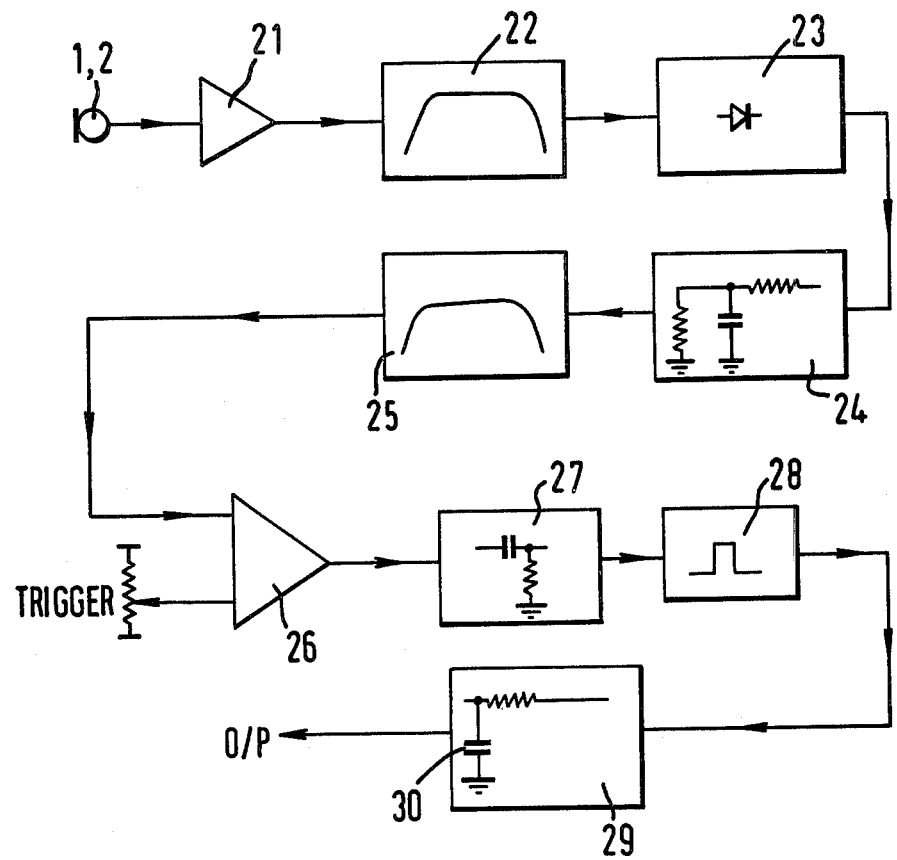
FIG. 2 is a block circuit diagram of part of the monitoring circuit of the apparatus shown in FIG. 1.

Operation of the monitoring unit 3, and associated speech detecting microphone 1,2 will now be described with reference to the circuit shown in FIG. 2. However, it should be noted firstly that the operation of this circuit is based upon the principle that, because all words contain at least one voiced syllable, the rate at which such syllables are detected provides a reasonably accurate indication of speech rate. The fact that comparatively long words may have two or more syllables or voiced components separated by unvoiced components does not matter, in that it is merely the rate at which the voiced components are detected. For instance, a long word with a number of voiced syllables when spoken quickly will give the same response as many single syllable words spoken quickly.

In operation of the apparatus, speech is detected by the microphone 1 and/or microphone 2 and the consequential speech signal is amplified in an amplifier 21. The amplified signal is then passed through a bandpass filter 22 (300–900 Hz), to eliminate extraneous noise and to permit only frequencies in the normal voice spectrum to be subsequently processed by the remaining components of the circuit. The filtered signal is then passed through a half-wave rectifier 23 and integrator 24. The resulting signal envelope, which has a predominently low frequency content, is now passed through a low frequency (5–10 Hz) bandpass filter 25 to remove large DC components from the signal envelope. This filtered signal envelope is then used to trigger a comparator 26 whose output is differentiated at 27 and used to trigger a monostable 28. The output of this monostable 28 is then integrated at 29 and, providing the charging and discharging times of the associated capacitor 30 are generally equal, the output of the integrator 29 will be proportional to the speech rate.

The integrator output signal can then be used to trigger a comparator, as long as such signal is greater than a predetermined speech signal rate, in which case it can be employed to actuate indicating means, such as the light source 4, meter 5, loudspeaker 6, earphone 7 or tactile indicator (not shown).

Alternatively, the output signal from the integrator 29 can be used to drive the meter 5 or other visual indicator, such as the light source 4, either directly or via a buffer circuit. Otherwise, the light source 4 could be driven directly from the monostable 28 to provide a continuous indication of the detection of each voiced syllable.

We claim:

1. Speech aiding apparatus comprising detecting means arranged to detect speech of a person to be monitored and to provide a speech signal representative of said speech, monitoring means responsive to said speech signal and arranged to determine the speech rate thereof and to provide an output signal only when said monitored speech signal rate exceeds a predetermined speech signal rate, means for adjusting said predetermined speech signal rate and indicating means having an input responsive to said output signal for providing an indication only when the monitored speech rate exceeds said predetermined speech rate.

2. Speech aiding apparatus as claimed in claim 1, in which said indicating means is a loudspeaker spaced from the ears of said person to be monitored.

3. A method of reducing disfluency of speech of a person suffering from speech disfluency, comprising detecting the speech of such a person, generating a speech signal representative thereof, monitoring said speech signal to determine the speech rate thereof and providing an output signal only when the speech rate of said monitored signal exceeds a predetermined speech rate, adjusting the value of the predetermined speech rate to suit the person being monitored, and using said output signal to actuate an indicating means only when the monitored speech rate exceeds said predetermined value.

4. A method as claimed in claim 3, and providing as said indicating means a loudspeaker that is spaced from the ears of said person.

* * * * *